US008372995B2

(12) United States Patent
Krishnan et al.

(10) Patent No.: US 8,372,995 B2
(45) Date of Patent: Feb. 12, 2013

(54) CRYSTALLINE SOLID FORMS OF TIGECYCLINE AND METHODS OF PREPARING SAME

(75) Inventors: Lalitha Krishnan, Suffern, NY (US); Subodh S. Deshmukh, White Plains, NY (US); Anthony Hadfield, St. Petersburg, FL (US); W. James Huang, Hillsborough, NJ (US); Mannching Sherry Ku, Thiells, NY (US)

(73) Assignee: Wyeth LLC, Madison, NJ (US)

( * ) Notice: Subject to any disclaimer, the term of this patent is extended or adjusted under 35 U.S.C. 154(b) by 1597 days.

(21) Appl. No.: 11/440,032

(22) Filed: May 25, 2006
(Under 37 CFR 1.47)

(65) Prior Publication Data

US 2007/0123497 A1    May 31, 2007

Related U.S. Application Data

(60) Provisional application No. 60/684,955, filed on May 27, 2005.

(51) Int. Cl.
*C07C 237/26* (2006.01)
*A61K 31/65* (2006.01)
*A61K 31/16* (2006.01)

(52) U.S. Cl. .................. 552/205; 514/152; 514/616
(58) Field of Classification Search .................. None
See application file for complete search history.

(56) References Cited

U.S. PATENT DOCUMENTS

| | | | | | |
|---|---|---|---|---|---|
| 5,675,030 | A | * | 10/1997 | Krishnan et al. | 552/205 |
| 2006/0247181 | A1 | * | 11/2006 | Fawzi et al. | 514/23 |
| 2007/0049560 | A1 | * | 3/2007 | Krishnan et al. | 514/152 |
| 2007/0049561 | A1 | * | 3/2007 | Krishnan et al. | 514/152 |
| 2007/0049562 | A1 | * | 3/2007 | Krishnan et al. | 514/152 |
| 2007/0049563 | A1 | * | 3/2007 | Krishnan et al. | 514/152 |

FOREIGN PATENT DOCUMENTS

| | | |
|---|---|---|
| EP | 0 536 515 | 4/1993 |
| EP | 0 582 788 | 2/1994 |
| EP | 0 582 789 | 2/1994 |
| EP | 0 582 790 | 2/1994 |
| EP | 0 582 810 | 2/1994 |

OTHER PUBLICATIONS

Brittain, H.G., 1999. Polmorphishms in Pharmaceutical Solids. Chapter 6 Methods for the Characterization of Polymorphs and Solutes. Marcel Decker, Inc., New York, NY, pp. 235-236.*
H. Brittain, ed. Polymorphism in Pharmaceutical Solids 1999, p. 235-236 (provided in Feb. 19, 2006 office action).*
USP-National Formulary, 1995. X-ray Diffraction, pp. 1834-1835 (provided by applicant in May 15, 2009 reply).*
Beidenbach et. al. "In vitro antimicrobial activity of GAR-936 tested against antibiotic-resistant gram-positive blood stream infection isolates and strains producing extended-spectrum beta-lactamases" Diagn. Microbiol. Infect. Dis. 40(4):173-7 (Aug. 2001).
Betrieu, C. et al. "In vitro activities of tigecycline against erythromycin-resistant *Streptococcus pyogenes* and *Streptococcus aglactiae*: mechanisms of macrolide and tetracycline resistance" Antimicrob. Agents Chemother. 48:323-5 (Jan. 2004).
Boothe, J.H. et al. "6-Deoxytetracyclines. I. Chemical modification by electrophilic substitution" J. Amer. Chem. Soc. 82:1253-4 (Mar. 5, 1960).
Boucher, H.W. et al., "In vitro activities of the glycylcycline GAR-936 against gram-positive bacteria" Antimicrob. Agents & Chemother. 44:2225-29 (2000).
Bradford, P.A. "Tigecycline: a first in class glycylcycline" Clin. Microbiol. Newsletter 26(21):163-8 (Nov. 1, 2004).
Hirata, T. et al. "Effects of efflux transporter genes on susceptibility of *Escherichia coli* to tigecycline (GAR-936)" Antimicrob. Agents Chemother. 48(6):2179-84 (Jun. 2004).
Hunter et al. "Tetracycline Antibiotic" Drugs of the Future 26:851-858 (2001).
International Search Report for PCT/US2006/20871 dated Nov. 13, 2006.
Milatovic, D. "Activities of the glycylcycline tigecycline (GAR-936) against 1,924 recent European clinical bacterial isolates" Antimicrob. Agents Chemother. 47(1):400-4 (Jan. 2003).
Patel, R. "In vitro activity of GAR-936 against vancomycin-resistant enterococci, methicillin-resistant *Staphylococcus aureus* and penicillin-resistant *Streptococcus pneumoniae*" Diagn. Microbiol. Infect. Dis. 38(3):177-9 (Nov. 2000).
Petersen, P.J. et al. "In vitro and in vivo activities of tigecycline (GAR-936), daptomycin, and comparative antimicrobial agents against glycopeptide-intermediate *Staphylococcus aureus* and other resistant gram-positive pathogens" Antimicrob. Agents Chemother. 46(8):2595-601 (Aug. 2002).
Petersen, P.J. et al. "In vitro and in vivo antibacterial activities of a novel glycylcycline, the 9-t-butylglycylamido derivative of minocycline (GAR-936)" Antimicrob. Agents Chemother. 43(4):738-44 (Apr. 1999).
Polymorphism in Pharmaceutical Solids, H. G. Brittain (ed.), 1999, p. 208.
Stephenson, G.A. et al. "Solid-state analysis of polymorphic, isomorphic, and solvated forms of dirithromycin" J. Amer. Chem. Soc. 116:5766-73 (1994).
Sum, P.-E. et al. "Synthesis and antibacterial activity of 9-substituted minocycline derivatives" Bioorg. Med. Chem. Lett. 16(2):400-3 (Jan. 15, 2006).
Sum, P.-E. et al. "Synthesis and structure-activity relationship of novel glycylcycline derivatives leading to the discovery of GAR-936" Bioorg. Med. Chem. Lett. 9(10):1459-62 (May 17, 1999).
Zhanel, G.G. et al. "The glycylcyclines: a comparative review with the tetracyclines" Drugs 64(1):63-88 (2004). Edelstein et al, "Activities of Tigecycline (GAR-936) against *Legionella pneumophila* In Vitro and in Guinea Pigs with L. pneumophila Pneumonia", Antimicrobial Agents and Chemotherapy, 47(2):533-540 (2003).
Wallace et al, "Comparison of the In Vitro Activity of the Glycylcycline Tigecycline (Formerly GAR 936) with Those of Tetracycline, Minocycline, and Doxycycline against Isolates of Nontuberculous Mycobacteria", Antimicrobial Agents and Chemotherapy, 46(10):3164-3167 (2002).

* cited by examiner

*Primary Examiner* — David J Blanchard
*Assistant Examiner* — Tigabu Kassa
(74) *Attorney, Agent, or Firm* — A. David Joran

(57) ABSTRACT

Crystalline solid forms of tigecycline, Form I, Form II, Form III, Form IV, and Form V, compositions comprising these crystalline solid forms, and processes for preparing these crystalline solid forms are described herein.

10 Claims, 9 Drawing Sheets

X-ray Powder Diffraction Pattern and Peak List of Form I Tigecycline

Peak Search Report (17 Peaks, Max P/N = 29.0)
[1634-026.RAW] Packed@ 0.25
PEAK: 27-pts/Parabolic Filter, Threshold=8.0, Cutoff=0.1%, BG=3/1.1, Peak-Top=Centroid Fit

| 2-Theta | d(A) | BG | Height | I% | Area | I% | FWHM |
|---|---|---|---|---|---|---|---|
| 5.225 | 16.8996 | 282 | 528 | 14.3 | 8103 | 11 | 0.261 |
| 8.292 | 10.6539 | 359 | 3681 | 100 | 73630 | 100 | 0.34 |
| 10.448 | 8.4599 | 385 | 944 | 25.6 | 20523 | 27.9 | 0.37 |
| 11.099 | 7.9652 | 398 | 565 | 15.3 | 10111 | 13.7 | 0.304 |
| 13.167 | 6.7185 | 385 | 1180 | 32.1 | 22730 | 30.9 | 0.327 |
| 13.666 | 6.4742 | 402 | 423 | 11.5 | 12999 | 17.7 | 0.522 |
| 14.657 | 6.0386 | 454 | 256 | 7 | 3889 | 5.3 | 0.258 |
| 15.596 | 5.6772 | 504 | 1588 | 43.1 | 30470 | 41.4 | 0.326 |
| 16.573 | 5.3445 | 487 | 491 | 13.3 | 9314 | 12.6 | 0.322 |
| 18.964 | 4.6757 | 567 | 612 | 16.6 | 19453 | 26.4 | 0.54 |
| 19.266 | 4.6032 | 460 | 595 | 16.2 | 37928 | 51.5 | 1.084 |
| 19.85 | 4.4691 | 664 | 531 | 14.4 | 7849 | 10.7 | 0.251 |
| 21.205 | 4.1864 | 590 | 964 | 26.2 | 24535 | 33.3 | 0.433 |
| 22.357 | 3.9732 | 678 | 1332 | 36.2 | 33274 | 45.2 | 0.425 |
| 23.085 | 3.8497 | 742 | 728 | 19.8 | 12485 | 17 | 0.292 |
| 24.772 | 3.5911 | 526 | 681 | 18.5 | 16499 | 22.4 | 0.412 |

X-ray Powder Diffraction Pattern and Peak List of Form II Tigecycline

Peak Search Report (17 Peaks, Max P/N = 34.4)
[1018-045.RAW] MSRD70-85 CRUDE PRE
PEAK: 27-pts/Parabolic Filter, Threshold=8.0, Cutoff=0.1%, BG=3/1.1, Peak-Top=Centroid Fit

| 2-Theta | d(A) | BG | Height | I% | Area | I% | FWHM |
|---|---|---|---|---|---|---|---|
| 9.219 | 9.5848 | 961 | 2296 | 40.8 | 70021 | 58.8 | 0.518 |
| 9.699 | 9.1115 | 1049 | 5630 | 100 | 119017 | 100 | 0.359 |
| 11.636 | 7.5987 | 935 | 298 | 5.3 | 3377 | 2.8 | 0.193 |
| 13.326 | 6.6385 | 921 | 976 | 17.3 | 26259 | 22.1 | 0.457 |
| 15.411 | 5.7448 | 1008 | 606 | 10.8 | 16940 | 14.2 | 0.475 |
| 17.664 | 5.0168 | 1223 | 761 | 13.5 | 12048 | 10.1 | 0.269 |
| 18.445 | 4.8062 | 1242 | 475 | 8.4 | 10795 | 9.1 | 0.386 |
| 19.826 | 4.4744 | 1443 | 3091 | 54.9 | 60837 | 51.1 | 0.335 |
| 20.415 | 4.3465 | 1596 | 1171 | 20.8 | 24994 | 21 | 0.363 |
| 21.446 | 4.1399 | 1688 | 3803 | 67.5 | 85696 | 72 | 0.383 |
| 22.314 | 3.9808 | 1832 | 733 | 13 | 12280 | 10.3 | 0.285 |
| 26.662 | 3.3407 | 894 | 622 | 11 | 15635 | 13.1 | 0.427 |
| 29.484 | 3.0271 | 919 | 1342 | 23.8 | 23203 | 19.5 | 0.294 |
| 30.657 | 2.9138 | 853 | 553 | 9.8 | 11720 | 9.8 | 0.36 |

X-ray Powder Diffraction Pattern and Peak List of Form III Tigecycline

Peak Search Report (14 Peaks, Max P/N = 13.4)
[L28094-21-3.txt]
PEAK: 27-pts/Parabolic Filter, Threshold=8.0, Cutoff=0.1%, BG=3/1.1, Peak-Top=Centroid Fit

| 2-Theta | d(A) | BG | Height | I% | Area | I% | FWHM |
|---|---|---|---|---|---|---|---|
| 5.229 | 16.8862 | 121 | 184 | 22.2 | 2426 | 28 | 0.224 |
| 5.95 | 14.8427 | 120 | 614 | 74.2 | 5824 | 67.2 | 0.161 |
| 8.294 | 10.6521 | 127 | 302 | 36.5 | 4006 | 46.2 | 0.226 |
| 9.319 | 9.4823 | 130 | 828 | 100 | 8671 | 100 | 0.178 |
| 10.551 | 8.3778 | 122 | 263 | 31.8 | 4158 | 48 | 0.269 |
| 11.834 | 7.4718 | 124 | 174 | 21 | 2803 | 32.3 | 0.274 |
| 13.132 | 6.7363 | 143 | 138 | 16.7 | 3689 | 42.5 | 0.454 |
| 13.69 | 6.4632 | 176 | 147 | 17.8 | 1445 | 16.7 | 0.167 |
| 14.384 | 6.1528 | 197 | 165 | 19.9 | 1374 | 15.8 | 0.142 |
| 14.951 | 5.9206 | 198 | 495 | 59.8 | 6991 | 80.6 | 0.24 |
| 15.505 | 5.7104 | 210 | 527 | 63.6 | 8664 | 99.9 | 0.279 |
| 17.758 | 4.9906 | 249 | 190 | 22.9 | 2374 | 27.4 | 0.212 |
| 21.376 | 4.1533 | 235 | 177 | 21.4 | 2884 | 33.3 | 0.277 |
| 24.773 | 3.591 | 177 | 188 | 22.7 | 3380 | 39 | 0.306 |

X-ray Powder Diffraction Pattern and Peak List of Form IV Tigecycline

Peak Search Report (24 Peaks, Max P/N = 30.1)
[L28094-16-3.txt]
PEAK: 27-pts/Parabolic Filter, Threshold=8.0, Cutoff=0.1%, BG=3/1.1, Peak-Top=Centroid Fit

| 2-Theta | d(A) | BG | Height | I% | Area | I% | FWHM |
|---|---|---|---|---|---|---|---|
| 4.633 | 19.0588 | 133 | 3744 | 100 | 29046 | 100 | 0.132 |
| 8.794 | 10.0471 | 60 | 621 | 16.6 | 5832 | 20.1 | 0.16 |
| 9.234 | 9.5696 | 61 | 629 | 16.8 | 5334 | 18.4 | 0.144 |
| 11.852 | 7.4608 | 72 | 155 | 4.1 | 1785 | 6.1 | 0.196 |
| 12.611 | 7.0133 | 60 | 318 | 8.5 | 4993 | 17.2 | 0.267 |
| 13.094 | 6.7556 | 67 | 972 | 26 | 13007 | 44.8 | 0.227 |
| 14.998 | 5.9022 | 55 | 195 | 5.2 | 3039 | 10.5 | 0.265 |
| 15.701 | 5.6396 | 83 | 1225 | 32.7 | 17693 | 60.9 | 0.246 |
| 16.101 | 5.5003 | 87 | 353 | 9.4 | 4307 | 14.8 | 0.207 |
| 16.784 | 5.2777 | 90 | 308 | 8.2 | 3179 | 10.9 | 0.175 |
| 18.017 | 4.9194 | 84 | 332 | 8.9 | 7203 | 24.8 | 0.369 |
| 19.505 | 4.5473 | 86 | 271 | 7.2 | 5530 | 19 | 0.347 |
| 19.92 | 4.4535 | 71 | 638 | 17 | 14798 | 50.9 | 0.394 |
| 20.364 | 4.3575 | 163 | 389 | 10.4 | 7685 | 26.5 | 0.336 |
| 21.22 | 4.1834 | 172 | 921 | 24.6 | 13867 | 47.7 | 0.256 |
| 21.954 | 4.0452 | 152 | 194 | 5.2 | 3989 | 13.7 | 0.35 |
| 22.942 | 3.8733 | 135 | 257 | 6.9 | 8656 | 29.8 | 0.573 |
| 23.416 | 3.7959 | 154 | 475 | 12.7 | 13374 | 46 | 0.479 |
| 24.401 | 3.6449 | 141 | 218 | 5.8 | 3117 | 10.7 | 0.243 |
| 25.325 | 3.514 | 114 | 146 | 3.9 | 2548 | 8.8 | 0.297 |
| 26.185 | 3.4005 | 133 | 151 | 4 | 3882 | 13.4 | 0.437 |

X-ray Powder Diffraction Pattern and Peak List of Form V Tigecycline

Peak Search Report (21 Peaks, Max P/N = 21.4)
[L28094-16-4.txt]
PEAK: 27-pts/Parabolic Filter, Threshold=8.0, Cutoff=0.1%, BG=3/1.1, Peak-Top=Centroid Fit

| 2-Theta | d(A) | BG | Height | I% | Area | I% | FWHM |
|---------|---------|-----|--------|------|-------|------|-------|
| 4.344 | 20.3237 | 149 | 1967 | 100 | 26846 | 100 | 0.232 |
| 8.622 | 10.2471 | 63 | 1014 | 51.6 | 12798 | 47.7 | 0.215 |
| 11.391 | 7.7618 | 55 | 330 | 16.8 | 3809 | 14.2 | 0.196 |
| 12.947 | 6.832 | 65 | 309 | 15.7 | 7631 | 28.4 | 0.42 |
| 13.199 | 6.7022 | 69 | 623 | 31.7 | 11380 | 42.4 | 0.311 |
| 14.918 | 5.9337 | 93 | 751 | 38.2 | 12236 | 45.6 | 0.277 |
| 15.472 | 5.7223 | 114 | 233 | 11.8 | 3950 | 14.7 | 0.288 |
| 16.208 | 5.4641 | 141 | 157 | 8 | 2044 | 7.6 | 0.221 |
| 16.588 | 5.3397 | 129 | 222 | 11.3 | 3274 | 12.2 | 0.251 |
| 17.263 | 5.1326 | 151 | 918 | 46.7 | 14272 | 53.2 | 0.264 |
| 18.917 | 4.6872 | 124 | 203 | 10.3 | 3203 | 11.9 | 0.268 |
| 19.913 | 4.4551 | 196 | 788 | 40.1 | 14316 | 53.3 | 0.309 |
| 20.504 | 4.3279 | 254 | 264 | 13.4 | 3221 | 12 | 0.207 |
| 21.054 | 4.2161 | 279 | 312 | 15.9 | 3668 | 13.7 | 0.2 |
| 21.569 | 4.1166 | 229 | 230 | 11.7 | 3268 | 12.2 | 0.242 |
| 22.038 | 4.03 | 241 | 180 | 9.2 | 2317 | 8.6 | 0.219 |
| 22.854 | 3.8879 | 159 | 602 | 30.6 | 11246 | 41.9 | 0.318 |
| 24.083 | 3.6923 | 117 | 261 | 13.3 | 4829 | 18 | 0.315 |
| 25.92 | 3.4345 | 168 | 263 | 13.4 | 5788 | 21.6 | 0.374 |

Overlay of X-ray Powder Diffraction Patterns of Forms I-V of Tigecycline

Expanded Overlay of X-ray Powder Diffraction Patterns of Forms I-V of Tigecycline Thermal Gravimetric Analysis (TGA) of Form II Tigecycline Thermal Gravimetric Analysis (TGA) Heat-Cool Cycle of Form II Tigecycline

CRYSTALLINE SOLID FORMS OF TIGECYCLINE AND METHODS OF PREPARING SAME

This application claims benefit of U.S. Provisional Application No. 60/684,955, filed May 27, 2005, the contents of which are incorporated herein by reference.

The present invention relates to crystalline solid forms of tigecycline, compositions thereof, and processes for preparing them.

Tigecycline is an antibiotic in the tetracycline family and a chemical analog of minocycline. It has been used as a treatment against drug-resistant bacteria, and has been shown to work where other antibiotics have failed. For example, it is active against methicillin-resistant *Staphylococcus aureus*, penicillin-resistant *Streptococcus pneumoniae*, vancomycin-resistant enterococci (D. J. Beidenbach et al., Diagnostic Microbiology and Infectious Disease 40:173-177 (2001); H. W. Boucher et al., Antimicrobial Agents & Chemotherapy 44:2225-2229 (2000); P. A. Bradford Clin. Microbiol. Newslett. 26:163-168 (2004); D. Milatovic et al., Antimicrob. Agents Chemother. 47:400-404 (2003); R. Patel et al., Diagnostic Microbiology and Infectious Disease 38:177-179 (2000); P. J. Petersen et al., Antimicrob. Agents Chemother. 46:2595-2601 (2002); and P. J. Petersen et al., Antimicrob. Agents Chemother. 43:738-744 (1999)), and organisms carrying either of the two major forms of tetracycline resistance: efflux and ribosomal protection (C. Betriu et al., Antimicrob. Agents Chemother. 48:323-325 (2004); T. Hirata et al. Antimicrob. Agents Chemother. 48:2179-2184 (2004); and P. J. Petersen et al., Antimicrob. Agents Chemother. 43:738-744 (1999)).

Tigecycline has historically been administered intravenously because it has exhibited generally poor bioavailability when given orally. The intravenous solution may be prepared by reconstitutution of an amorphous powder with sterile water, 0.9% Sodium Chloride Injection, USP, or 5% Dextrose Injection, USP. Tigecycline is typically rendered into the amorphous powder via lyophilization without excipients for sterilization purposes. Due to the propensity for tigecycline to degrade, however, these powders are prepared and processed under low-oxygen and low-temperature conditions. Such processing is expensive because it requires special equipment and handling. Additionally, amorphous materials are generally less stable than crystalline forms of the same compound. (Polymorphism in Pharmaceutical Solids, H. G. Brittain (ed.), 1999, p. 208). It would be advantageous, therefore, if one were able to use and manufacture crystalline solid forms of tigecycline without the need for special handling systems.

Crystalline compounds are solids with ordered arrays of molecules, whereas amorphous compounds are composed of disordered molecules. These arrays are also termed crystal lattices and are composed of repeating structural segments called unit cells. When the same molecule, such as an organic molecule, can order itself in a solid in more than one way, that molecule exhibits what is called polymorphism. For example, the element carbon exhibits polymorphism (in elements it is termed allotropism). Solid carbon exists in three known crystalline solid forms: graphite, diamond, and fullerenes. Although each crystalline solid form is carbon, each has different properties because the solid-state structure of each form differs. For example, whereas diamond is one of the hardest substances known, graphite is extremely soft. Many organic compounds are also known to be polymorphic in that their structures differ in how they pack together to form crystalline solids. (See e.g., Stephenson, G. A; Stowell, J. G; Toma, P. H; Dorman, D. E.; Greene, J. R.; Byrne, S. R.; "Solid state analysis of polymorphic, isomorphic and solvated forms of Dirithromycin", J. Am. Chem. Soc., 1994,116, 5766.)

Based on a chemical structure, which is the chemical connectivity of atoms to make a molecule, one cannot predict with any degree of certainty whether a compound will crystallize, under what conditions it will crystallize, how many crystalline solid forms of the compound might exist, or the solid-state structure of any of those forms. The term "solid-state structure" as used herein means the structure obtained when molecules pack together to form a solid.

Sometimes solvent or water molecules become incorporated into the crystal lattice of a crystalline solid. Such a crystalline solid may be referred to as a solvate or hydrate, respectively. Solvates, hydrates, and polymorphs are often called crystalline solid forms. Here, as in most of the solid-state chemical arts, weakly bound solvates and hydrates are also included as crystalline solid forms where the solvent or water molecules are in channels or not incorporated into the crystal lattice. Amorphous forms are often referred to as solid forms but they are not crystalline solid forms.

Different crystalline solid forms of the same compound often possess different solid-state properties such as melting point, solubility, handling, and stability. Thus, once different crystalline solid forms of the same compound have been identified, the optimum crystalline solid form under any given set of processing and manufacturing conditions may be determined as well as the different solid-state properties of each crystalline solid form.

There are a number of analytical methods one of ordinary skill in the art in solid-state chemistry can use to analyze solid forms. The term "analyze" as used herein means to obtain information about the solid-state structure of solid forms. For example, X-ray powder diffraction is a suitable technique for differentiating amorphous solid forms from crystalline solid forms and for characterizing and identifying crystalline solid forms of a compound. X-ray powder diffraction is also suitable for quantifying the amount of a crystalline solid form (or forms) in a mixture. In X-ray powder diffraction, X-rays are directed onto a crystal and the intensity of the diffracted X-rays is measured as a function of twice the angle between the X-ray source and the beam diffracted by the sample. The intensity of these diffracted X-rays can be plotted on a graph as peaks with the x-axis being twice the angle (this is known as the "2θ" angle) between the X-ray source and the diffracted X-rays and with the y-axis being peak intensity of the diffracted X-rays. This graph is called an X-ray powder diffraction pattern or powder pattern. Different crystalline solid forms exhibit different powder patterns because the location of the peaks on the x-axis is a property of the solid-state structure of the crystal.

Such powder patterns, or portions thereof, can be used as an identifying fingerprint for a crystalline solid form. Thus, one could take a powder pattern of an unknown sample and compare that powder pattern with a reference powder pattern. A positive match would mean that the unknown sample is of the same crystalline solid form as that of the reference. One could also analyze an unknown sample containing a mixture of solid forms by adding and subtracting powder patterns of known compounds.

When selecting peaks in a powder pattern to characterize a crystalline solid form or when using a reference powder pattern to identify a form, one identifies a peak or collection of peaks in one form that are not present in the other solid forms.

The term "characterize" as used herein means to select an appropriate set of data capable of distinguishing one solid form from another. That set of data in X-ray powder diffraction is the position of one or more peaks. Selecting which tigecycline X-ray powder diffraction peaks define a particular form is said to characterize that form.

The term "identify" as used herein means taking a selection of characteristic data for a solid form and using those data to determine whether that form is present in a sample. In X-ray powder diffraction, those data are the x-axis positions of the one or more peaks characterizing the form in question as discussed above. For example, once one determines that a select number of X-ray diffraction peaks characterize a particular solid form of tigecycline, one can use those peaks to determine whether that form is present in a sample containing tigecycline.

When characterizing and/or identifying crystalline solid forms of the same chemical compound with X-ray powder diffraction, it is often not necessary to use the entire powder pattern. A smaller subset of the entire powder pattern can often be used to perform the characterization and/or identification. By selecting a collection of peaks that differentiate the crystalline solid form from other crystalline solid forms of the compound, one can rely on those peaks to both characterize the form and to identify the form in, for example, an unknown mixture. Additional data can be added, such as from another analytical technique or additional peaks from the powder pattern, to characterize and/or identify the form should, for instance, additional polymorphs be identified later.

Due to differences in instruments, samples, and sample preparation, peak values are reported with the modifier "about" in front of the peak values. This is common practice in the solid-state chemical arts because of the variation inherent in peak values. A typical precision of the 2θ x-axis value of a peak in a powder pattern is on the order of plus or minus 0.2° 2θ. Thus, a powder diffraction peak that appears at "about 9.2° 2θ," means that the peak could be between 9.0° 2θ and 9.4° 2θ when measured on most X-ray diffractometers under most conditions. Variability in peak intensity is a result of how individual crystals are oriented in the sample container with respect to the external X-ray source (known as "preferred orientation"). This orientation effect does not provide structural information about the crystal.

X-ray powder diffraction is just one of several analytical techniques one may use to characterize and/or identify crystalline solid forms. Spectroscopic techniques such as Raman (including microscopic Raman), infrared, and solid-state NMR spectroscopies may be used to characterize and/or identify crystalline solid forms. These techniques may also be used to quantify the amount of one or more crystalline solid forms in a mixture.

Thermal techniques such as melting point do not necessarily, in and of themselves, characterize and/or identify different crystalline solid forms of a compound because it is possible that different crystalline solid forms of the same compound would have indistinguishable melting points. In such circumstances, however, melting points could be used together with another analytical method, such as X-ray powder diffraction, to characterize and/or identify crystalline solid forms.

The present invention is directed to crystalline solid forms of tigecycline identified as Form I, Form II, Form III, Form IV, and Form V. The invention is also directed to compositions, including pharmaceutical compositions, containing one or more crystalline solid forms of tigecycline. The invention is further directed to processes for preparing crystalline solid forms of tigecycline.

DETAILED DESCRIPTION OF THE INVENTION

Two X-ray diffractometers were used in the work leading to the present invention. The data in FIG. 1 and FIG. 2 were collected using a Rigaku Miniflex Diffraction System (Rigaku MSC Inc., Tokyo, Japan). The powder samples were deposited on a zero-background polished silicon sample holder. A normal focus copper X-ray tube is operated at 30 kV and 15 mA, and the instrument is equipped with a Ni Kβ filter. Sample scanning is at 0.02°/step from 3.00 to 40.00° 2θ. The data processing is done using Jade 6.0 software (Molecular Data Systems Inc., Livermore, Calif.). The data in FIG. 3 and FIG. 4, and FIG. 5 were collected using a Scintag Advanced Diffraction System Model X2 (Scintag, Inc. Cupertino, Calif.) with a quartz sample holder. The copper X-ray generator is operated at 45 kV and 40 mA, and scanning is done from 3 to 40° 2θ at 0.02° per step. Data processing is done using Jade 6.0 software (Molecular Data Systems). FIGS. 1-5 each contains two parts: a peak-picked X-ray powder diffractogram and a peak list. The peak lists were generated using standard parameters and commercial software.

Figure 1:
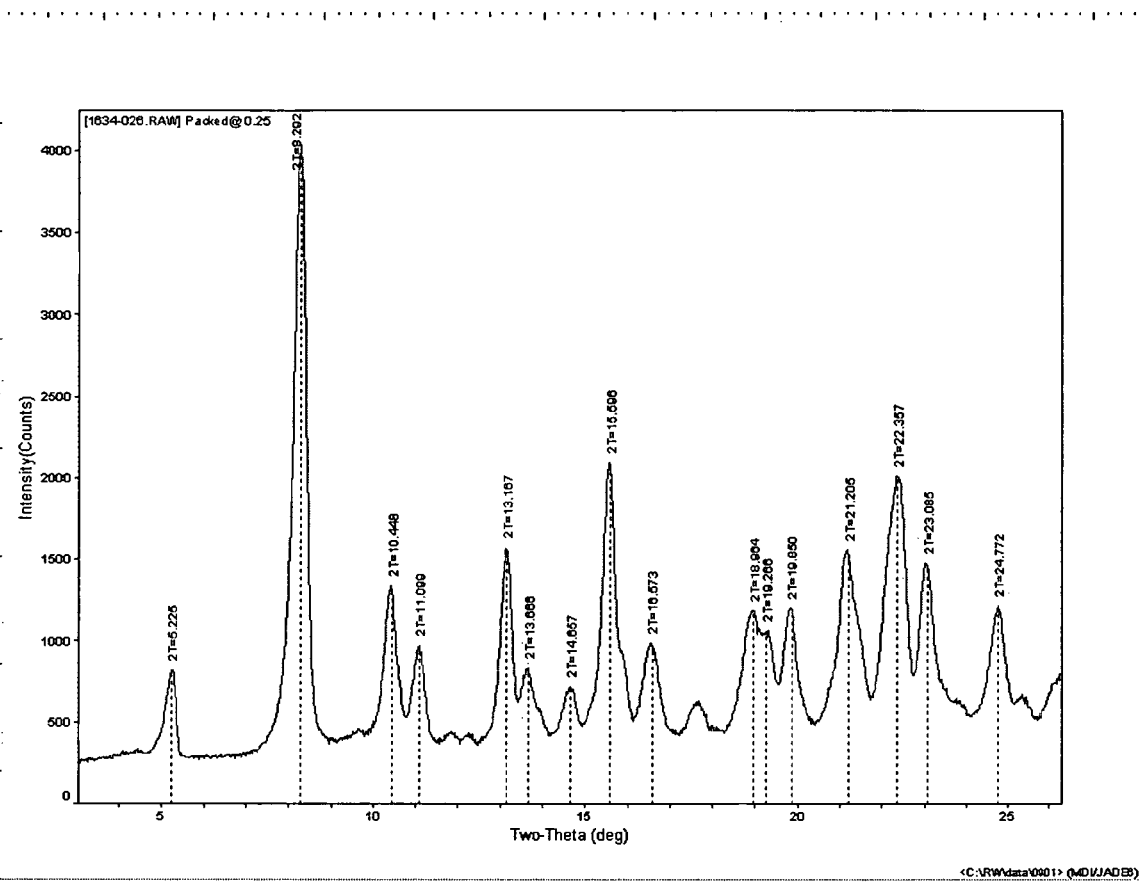
FIG. 1 is the X-ray powder diffraction pattern and peak list for Form I tigecycline.
Figure 2:
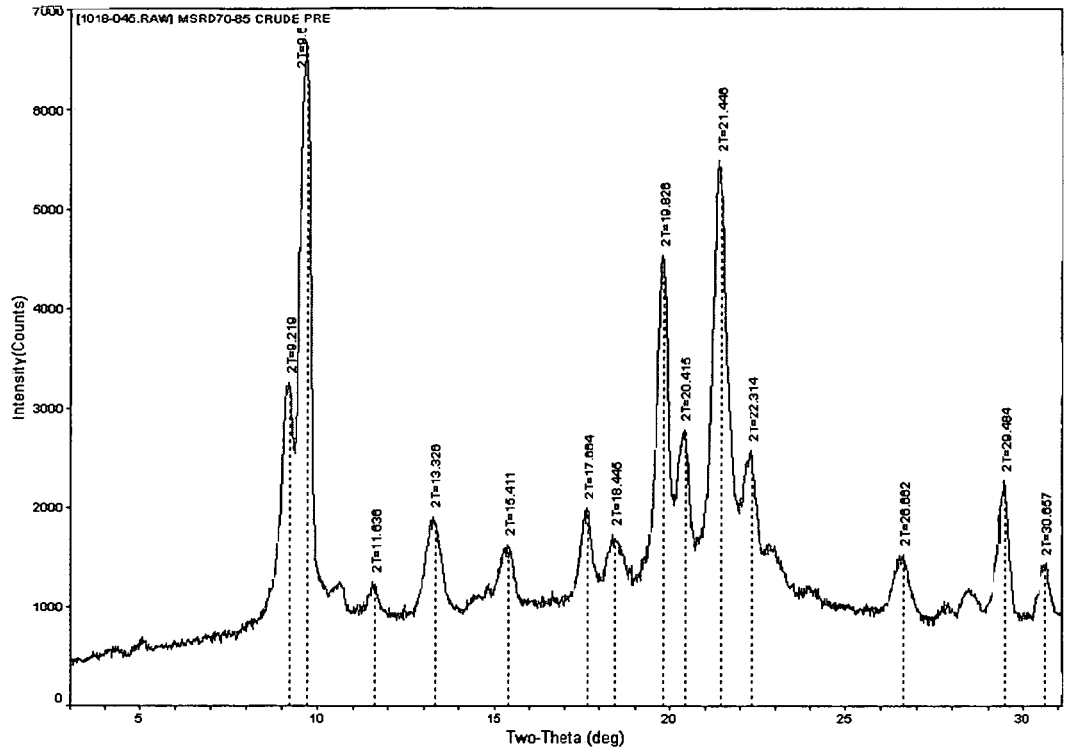
FIG. 2 is the X-ray powder diffraction pattern and peak list for Form II tigecycline.
Figure 3:
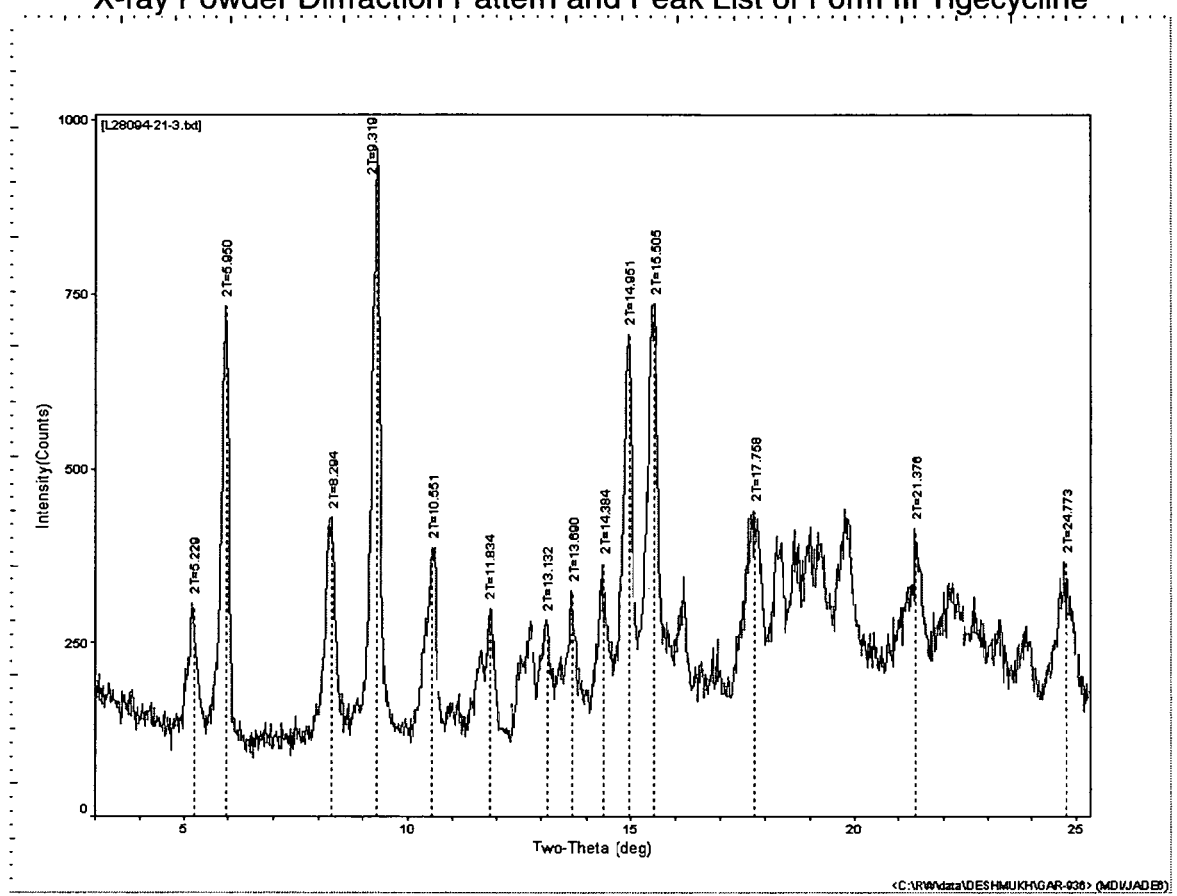
FIG. 3 is the X-ray powder diffraction pattern and peak list for Form III tigecycline.
Figure 4:
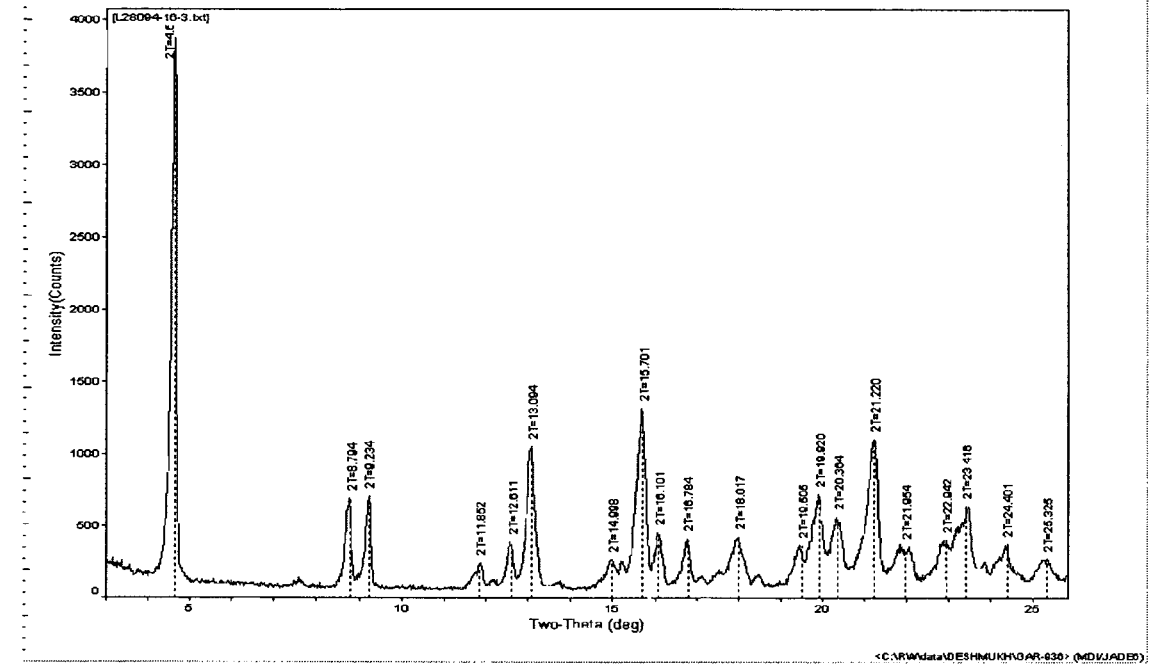
FIG. 4 is the X-ray powder diffraction and peak list for Form IV tigecycline.
Figure 5:
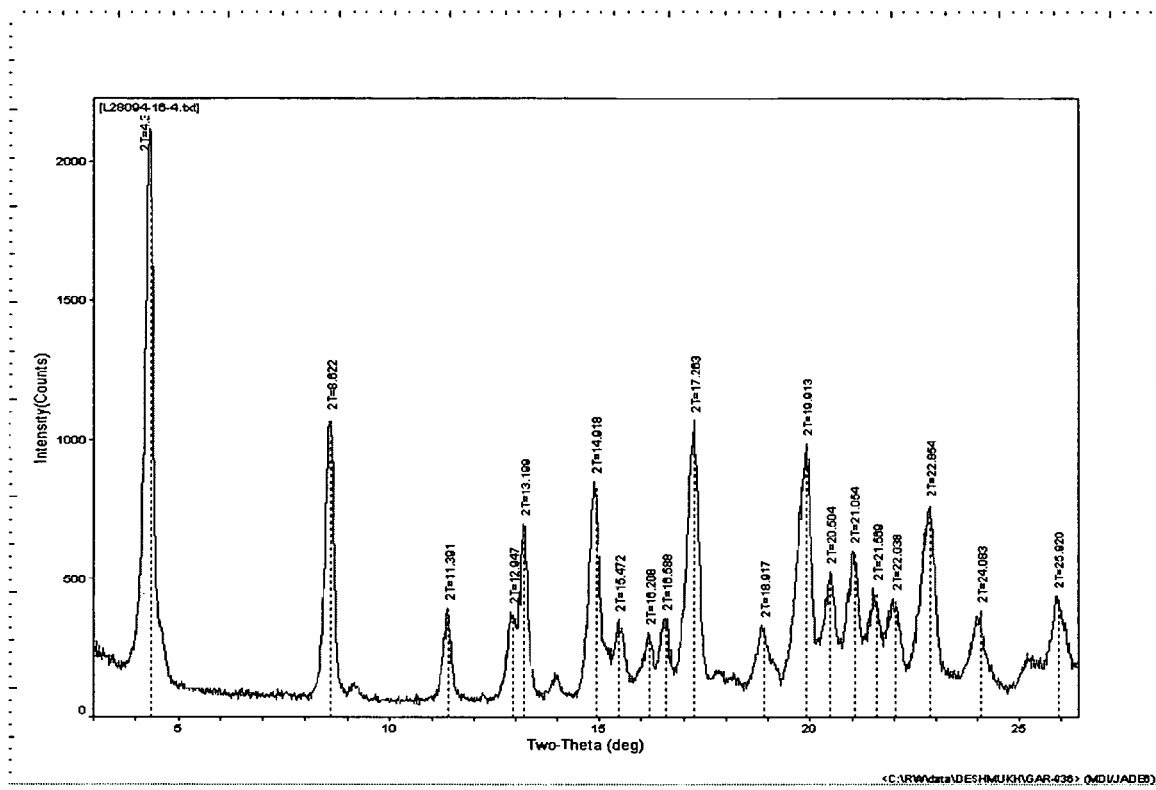
FIG. 5 is the X-ray powder diffraction and peak list for Form V tigecycline.
Figure 6:
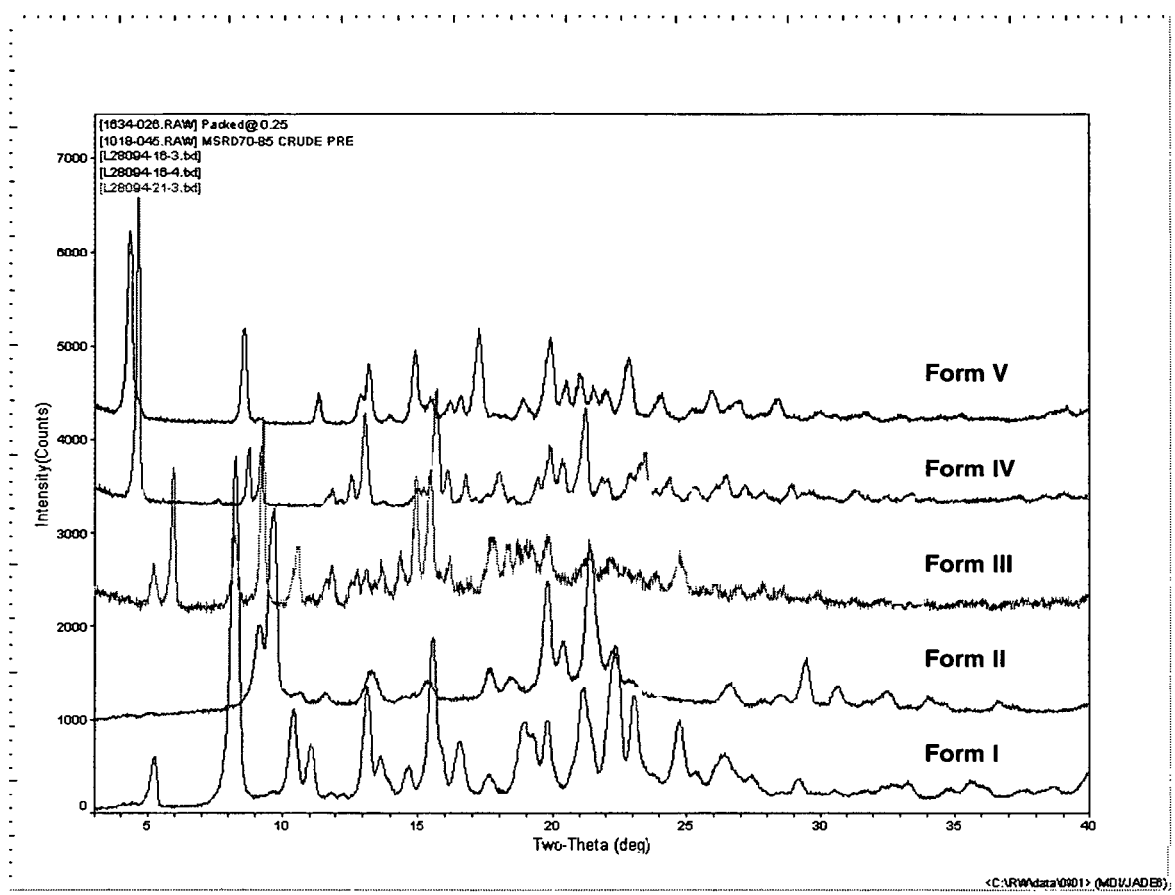
FIG. 6 is an X-ray powder diffraction overlay of Forms I-V of tigecycline.

When those of ordinary skill in the solid-state chemistry art analyze powder patterns to discern whether the seemingly different patterns actually represent different crystalline solid forms, they often overlay the powder patterns on, for example, a light box or on a computer screen. An example of just such an overlay can be found at FIG. 6 which is the overlay representing the five crystalline solid forms of tigecycline that were characterized and identified. An expanded version of the overlay is at FIG. 7.

The entire X-ray powder diffraction may be used to characterize each crystalline solid form of tigecycline, however, one may select a smaller subset of peaks in each pattern to characterize each crystalline solid form of tigecycline. Those selected peaks may then be used to identify the presence of particular crystalline solid forms of tigecycline in an unknown sample of or containing tigecycline.

To illustrate, Table 1 lists the first 6 peaks in the diffractograms of Form I and Form II.

TABLE 1

| Tigecycline Form | ° 2θ | ° 2θ | ° 2θ | ° 2θ | ° 2θ | ° 2θ |
| --- | --- | --- | --- | --- | --- | --- |
| Form I | 5.2 | 8.3 | 10.4 | 11.1 | 13.2 | 13.7 |
| Form II | 9.2 | 9.7 | 11.6 | 13.3 | 15.4 | 17.7 |

Based on a comparison of these data, and only considering these two forms of tigecycline, it is apparent that one could rely on the 6 listed Form I peaks to characterize Form I because the collection of 6 peaks is not present to +0.2° 2θ in Form II. However, it is not necessary to rely on all 6 peaks to conclude that Form I differs from Form II. In fact, the single peak at about 5.2° 2θ in Form I uniquely characterizes Form I because the nearest Form II peak to about 5.2° 2θ is found at about 9.2° 2θ, 4 degrees 2θ away. This 4° 2θ difference is significantly greater than the 0.4° 2θ obtained by combining the variability (0.2° 2θ) in any two peaks. In other words, so long as a peak in one sample is more than 0.4° 2θ away from any peak in another sample, then those represent different crystalline solid forms because the chance that any given peak in a crystalline solid form would vary by more than 0.4° 2θ from sample to sample and/or instrument to instrument is extremely small. Therefore, in a system that contains only Form I and Form II, a tigecycline powder pattern containing a peak at about 5.2° 2θ characterizes Form I tigecycline and the presence of that peak may be used to identify Form I. Similarly, when characterizing Form II, one could use just the peak at about 9.2° 2θ because there is no Form I peak within 0.4° 2θ of that peak.

Not all peaks in Table 1 could be used to characterize Form I. For example, the peak at about 13.2° 2θ in Form I could not in and of itself be used to characterize Form I because Form II possesses a peak at about 13.3° 2θ which is only 0.1° 2θ away.

In accordance with the invention, X-ray powder diffraction data were collected on the five crystalline tigecycline forms, Forms I, II, III, IV, and V, and the peaks below around 26° 2θ appear in Table 2. It is determined that peaks of higher intensity were more susceptible to preferred orientation effects. Furthermore, the peaks listed in Table 2 were selected by considering the peak lists in FIGS. 1-5. Thus, the data in Table 2 may be used to find the subsets of peaks to characterize and/or identify the crystalline solid forms of tigecycline that are the subject of the present invention.

TABLE 2

Forms (peaks listed in ° 2θ)

| I | II | III | IV | V |
|---|---|---|---|---|
| 5.2 | 9.2 | 5.2 | 4.6 | 4.3 |
| 8.3 | 9.7 | 6.0 | 8.8 | 8.6 |
| 10.4 | 11.6 | 8.3 | 9.2 | 11.4 |
| 11.1 | 13.3 | 9.3 | 11.9 | 12.9 |
| 13.2 | 15.4 | 10.6 | 12.6 | 13.2 |
| 13.7 | 17.7 | 11.8 | 13.1 | 14.9 |
| 14.7 | 18.4 | 13.1 | 15.0 | 15.5 |
| 15.6 | 19.8 | 13.7 | 15.7 | 16.2 |
| 16.6 | 20.4 | 14.4 | 16.1 | 16.6 |
| 19.0 | 21.4 | 15.0 | 16.8 | 17.3 |
| 19.3 | 22.3 | 15.5 | 18.0 | 18.9 |
| 19.9 | | 17.8 | 19.5 | 19.9 |
| 21.2 | | 21.4 | 19.9 | 20.5 |
| 22.4 | | 24.8 | 20.4 | 21.1 |
| 23.1 | | | 21.2 | 21.6 |
| 24.8 | | | 22.0 | 22.0 |
| | | | 22.9 | 22.9 |
| | | | 23.4 | 24.1 |
| | | | 24.4 | 25.9 |
| | | | 25.3 | |

In accordance with the invention, because none of the peaks listed for Form I is greater than 0.4° 2θ from every other peak of each of Forms II, III, IV, and V, no single Form I peak characterizes Form I from each of Forms II, III, IV, and V. For example, whereas the peak at about 5.2° 2θ in Form I could be used to distinguish between Form I and Form II, it alone could not be used to distinguish between Form I and Form III because Form III also has a peak at 5.2° 2θ. However, the subset of Form I peaks at about 5.2° 2θ and about 11.1° 2θ could be used to distinguish Form I from both Form II and Form III because the peak at about 11.1° 2θ is more than 0.4° 2θ from any peak in Form III. By the same reasoning, the peak at 5.2° 2θ could also be used to distinguish Form I from Form IV and Form V. Thus, X-ray diffraction peaks at about 5.2° 2θ and about 11.1° 2θ are characteristic of Form I and may be used to identify Form I in a sample. In characterizing and identifying Form I, one may also rely on some or all of the other peaks from the Form I powder pattern peak list in FIG. 1.

A similar analysis is done for Forms II, III, IV, and V to construct sets of characteristic X-ray powder diffraction peaks that can be used to characterize and identify the different crystalline solid forms of tigecycline of the present invention.

In accordance with the invention, with respect to Form II, the peak at about 9.2° 2θ distinguishes Form II from Form I and Form V. It does not, in and of itself, however, distinguish Form II from Form III or from Form IV. The peak at about 9.7° 2θ is distinguishable over Form IV, but is 0.4° 2θ from a peak in Form III. The peak at about 20.4° 2θ in Form II distinguishes it from Form III. Therefore, Form II peaks at about 9.2° 2θ, about 9.7° 2θ, and about 20.4° 2θ distinguish Form II over Forms I, III, IV, and V and thus characterize Form II in a sample. Further, these peaks make be used to identify Form II. In characterizing and identifying Form II, one may also rely on some or all of the other peaks from the Form II powder pattern peak list in FIG. 2.

In accordance with the invention, in Form III, the peak at about 6.0° 2θ distinguishes Form III over Forms I, II, IV, and V and further characterizes Form III. Further, this peak may be used to identify Form III in a sample. In characterizing and identifying Form III, one may also rely on some or all of the other peaks from the Form III powder pattern peak list in FIG. 3.

In accordance with the invention, in Form IV, the peak at about 4.6° 2θ distinguishes Form IV over Forms I, II, and III, and the peak at about 9.2° 2θ is more than 0.4° 2θ from peaks in Form V. Thus, peaks at about 4.6° 2θ and about 9.2° 2θ distinguish Form IV from Forms I, II, III, and V and thus characterize Form IV. Further, these peaks may be used to identify Form IV in a sample. In characterizing and identifying Form IV, one may also rely on some or all of the other peaks from the Form IV powder pattern peak list in FIG. 4.

In accordance with the invention, for Form V, the peak at about 4.3° 2θ distinguishes Form V from Forms I, II, and III. The Form V peak at 11.4° 2θ further distinguishes Form V from Form IV. Thus, peaks at about 4.3° 2θ and about 11.4° 2θ distinguish Form V over Forms I, II, III, and IV and therefore characterize Form V. Further, these peaks may be used to identify Form V in a sample. In characterizing and identifying Form V, one may also rely on some or all of the other peaks from Form V powder pattern peak list in FIG. 5.

Other analytical techniques may also be useful in analyzing crystalline solid forms of tigecycline. Spectroscopic techniques such as Raman (including microscopic Raman), infrared, and solid-state NMR spectroscopies may be used to characterize and/or identify crystalline solid forms. These techniques may also be used to quantify the amount of one or more crystalline solid forms in a mixture.

Table 3 sets forth data showing melting point onset by hot stage microscopy of several samples of Forms I, II, III, IV and V of the invention. Thermal techniques, such as melting point onset by hot stage microscopy, do not necessarily, in and of themselves, characterize or identify the different crystalline solid forms of tigecycline based on the data shown in Table 3. For example, Form I and Form IV each include a measured melting point onset by hot stage microscopy of about 170° C.

and thus cannot be distinguished from one another by this technique. In contrast, Form III is distinguishable from Form V by using this technique because Form V has a melting point onset by hot stage at about 174° C. and Form III at about 167° C. Melting point onsets by hot stage microscopy may be used together with another analytical method, such as X-ray powder diffraction, to characterize and/or identify crystalline solid forms of tigecycline.

TABLE 3

| Tigecycline Form | Melting Point Onset by Hot Stage Microscopy |
| --- | --- |
| Form I (3 samples) | 170° C., 172° C., 172° C. |
| Form II | 169° C. |
| Form III | 167° C. |
| Form IV | 170° C. |
| Form V | 174° C. |

In the hot stage microscopy measurements, the stage temperature for the hot stage microscope is controlled by a Creative Devices, Inc (Neshanic Station, N.J.), Model 50-600 Controller. The sample heating rate is 10° C./min. The microscope used is a Nikon (Tokyo, Japan) DIAPHOT 300 system. Images were processed with the Image-Pro Plus software. Melting point onset values are reported with the modifier "about," which is standard terminology in the solid-state chemical arts and is meant to account for changes in melting point due to the presence of water, solvent, or chemical impurities, as well as variability introduced into melting point measurements by the analytical instrument and methodology employed.

Figure 7:
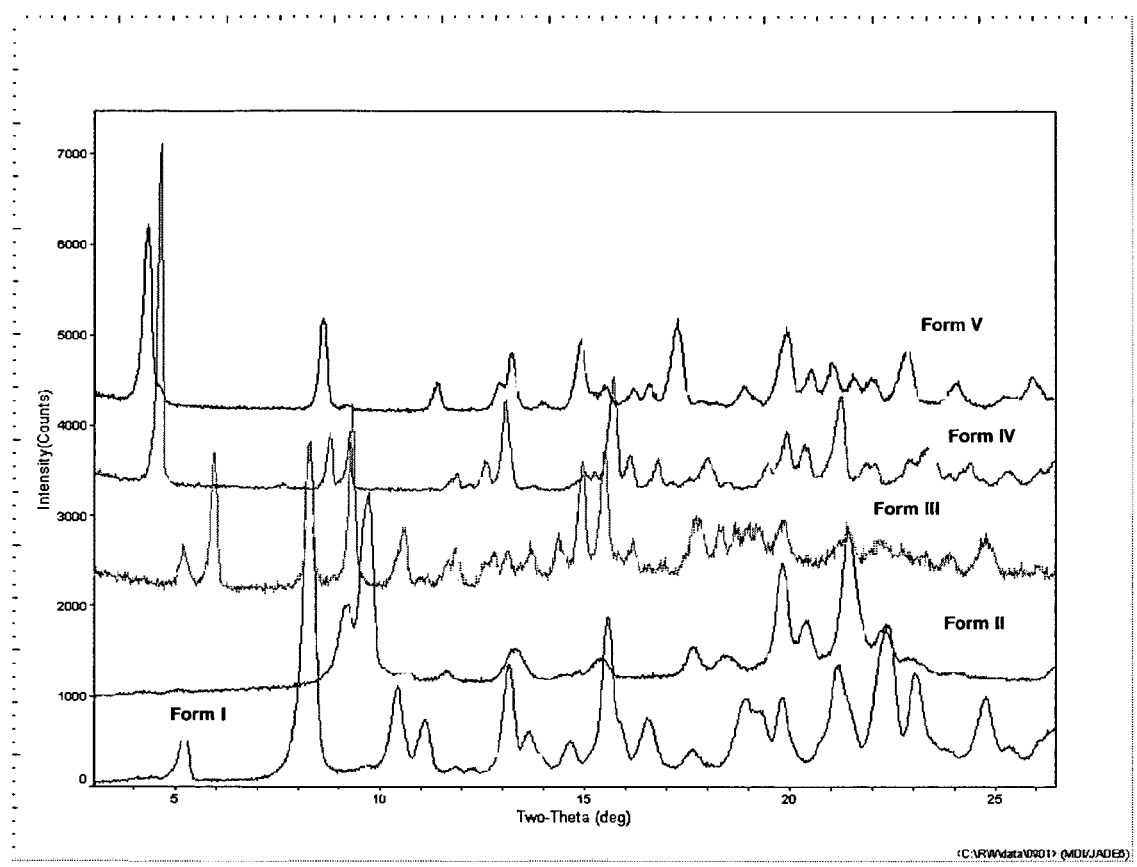
FIG. 7 is an expanded version of the X-ray powder diffraction overlay of Forms I-V of tigecycline.
Figure 8:
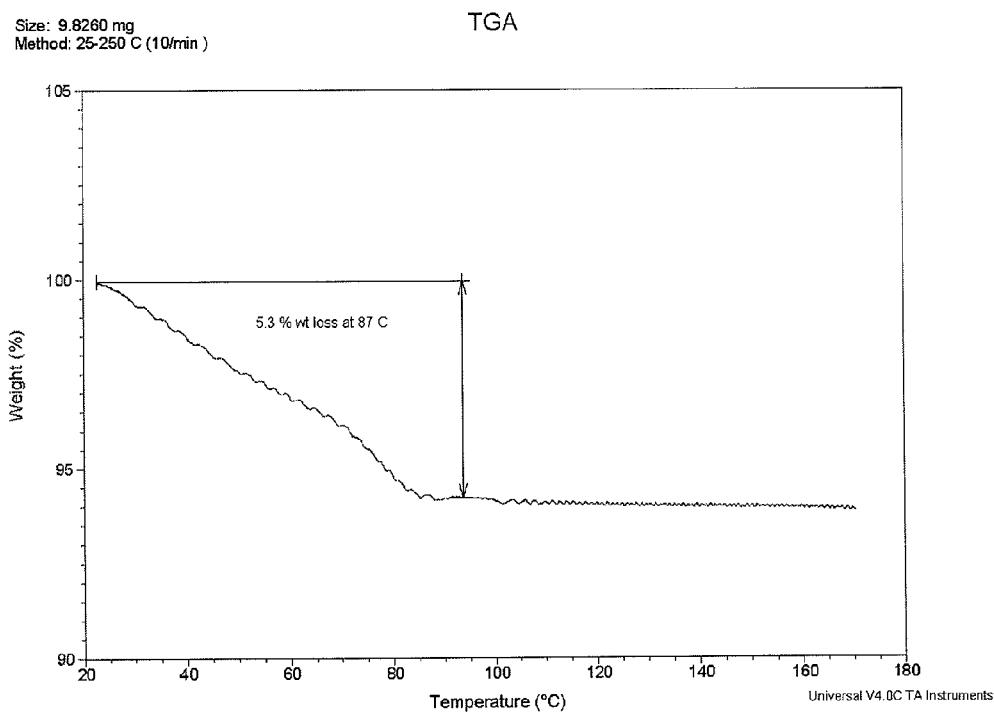
FIG. 8 is a thermal gravimetric analysis ("TGA") of Form II tigecycline.

Thermal measurements by a TA Instruments (New Castle, Del.) thermal gravimetric analysis ("TGA") indicate that Form II is a hydrate. In FIG. 7, Form II exhibited a weight loss of about 5.3% when a Form II sample is heated at 10° C./minute beginning from between approximately 25° C. to approximately 100° C. That the majority of this weight loss is likely due to water is further indicated by a heat-cool cycle TGA experiment in FIG. 8. In such a cycle, the sample is heated first to about 55° C. and then cooled to about 37° C. and heated again, cooled, and heated again. Weight loss of about 4.4% is observed in the first heat-cool cycle, with little weight loss observed in the subsequent cycles. This weight loss behavior in a heat-cool cycle, where substantially no further weight loss is observed after the first cycle, is consistent with the sample being a hydrate. Thus, Form II is believed to be a hydrate with a hydration level of about 4.4%.

That tigecycline crystallizes into five different crystalline solid forms could not have been predicted from the tigecycline chemical formula. Nor would it have been possible to predict the structure or properties of any of the crystalline solid forms. The five crystalline solid forms of tigecycline of the invention were prepared by determining the appropriate set of conditions that would enable those forms to crystallize.

The present invention also provides processes for making crystalline solid forms of tigecycline. By slurrying Form I in organic solvents under varying conditions, Forms II-V can be prepared. In the slurries, Form I is treated with one or more organic solvents in such amounts wherein the solid Form I did not completely dissolve and mixed in the solvent or mixtures of solvents for some period of time as a slurry. Sometimes, the slurries were heated and on other occasions the slurries were treated with another solvent. Prior to analysis, the slurries were filtered to isolate the solid, followed by drying under vacuum. The resulting solids could then be analyzed by a number of analytical techniques.

Where it has been determined that a solvent can aid in converting the starting form into another form, that solvent is referred to herein as a "suitable solvent" for that conversion. For example, it is determined that by slurrying Form I in dichloromethane, Form I is converted into Form III. Therefore, dichloromethane is a suitable solvent for that conversion. Also, Form I can be converted to Form III by crystallizing from tetrahydrofuran (THF) and stirring with dichloromethane. Form II can be generated by slurrying Form I in methanol. Accordingly, methanol is a suitable solvent for that conversion. Optionally, Form II can be generated by slurrying Form I in methanol/dichloromethane wherein the methanol content is greater than 10%. Likewise, Form I is converted into Form IV by slurrying Form I in acetonitrile. Thus, acetonitrile is a suitable solvent for that conversion. Further, slurrying Form I in acetonitrile/n-heptane generates Form IV. Additionally, slurrying Form I in tetrahydrofuran results in the conversion of Form I into Form V. As a result, tetrahydrofuran is a suitable solvent for that conversion. Slurrying of form I in the acetone/methanol (1:1 v/v) results in form I as does crystallization from acetone/methanol.

In addition to slurrying, other treatments with suitable solvents can afford the conversion of one form to another. For example, tigecycline Form II can be prepared by crystallizing tigecycline out of methanol. Additionally, tigecycline Form II can be prepared by the slow addition of methanol to a solution of tigecycline in water which gives Form II particles >20 μm. Further, by the addition of a solution of tigecycline in water to methanol gives Form II particles which are <20 μm. Accordingly, methanol, methanol/water or water/methanol are suitable for the formation of Form II by crystallizing tigecycline.

Particle length data is collected from optical images of tigecycline particles. Optical microscopy analysis is performed using a Nikon Eclipse E600 microscope capable of 5× to 100× magnification, fitted with a digital camera (Nikon DXM 1200) and a calibrated image acquisition system (Nikon ACT-1 v 2.12). Images are processed using ImagePro plus image processing software (Media Cybernetics, Silver Spring, Md.). The software used a contrast-differentiation algorithm to isolate tigecycline particles from a uniform background. The results of data analysis is shown in the following Table 4.

TABLE 4

| | Particle length | | |
| --- | --- | --- | --- |
| Sample | Mean microns | Median microns | $90^{th}$ percentile microns |
| Addition of methanol to an aqueous solution of tigecycline | 22.67 | 18.16 | 47.87 |
| Addition of an aqueous solution of tigecycline to methanol | 7.28 | 3.97 | 18.1 |

Form III can be obtained by crystallizing tigecycline out of dichloromethane. Form IV can be obtained by crystallizing tigecycline out of acetonitrile, and Form V can be obtained by crystallizing tigecycline out of tetrahydrofuran.

In accordance with the invention, formulations of tigecycline for use in animals or humans can be made from Forms I-V of the invention. The solubilities of the five crystalline solid forms of tigecycline are all greater than 25 mg/ml in water, thus they are all expected to be bioequivalent with one another.

Pharmaceutical compositions for parenteral use can also be prepared with any of Forms I-V with or without a lyophilization step. Pharmaceutical compositions of crystalline tigecycline using one or more of Forms I-V can also be prepared in accordance with the invention. Such compositions can be used to deliver pharmaceutically effective amounts of one or more of Forms I-V of tigecycline. The composition may comprise the crystalline form of tigecycline in combination or association with a pharmaceutically suitable carrier.

The following non-limiting examples illustrate several methods of making Forms I-V of tigecycline.

EXAMPLE 1

Preparation of Form I 300 grams of crude 9-chloroacetamidominocycline is added at room temperature (25-28° C.) slowly with efficient stirring to 2000 mL of t-butylamine in a 5 liter three-necked round-bottom flask fitted with a stirrer and thermometer. Forty-eight grams of sodium iodide is added and the reaction mixture is stirred at 35-40° C. for 6 hours. The reaction is monitored by HPLC and when <2% starting material remained, it is treated with 500 mL of methanol and the solvent is stripped off on a rotary evaporator at 40° C. To the residue is added 1100 mL of methanol and 1700 mL of water. The solution is cooled to 0-2° C. and adjusted to pH 7.2 with concentrated HCl (~250 mL). The total volume of the reaction mixture at this point is 3500 mL. It is diluted to 8.5 liters with water and the pH adjusted to 4.0-4.2 with concentrated HCl (12 mL). 1.6 kg of washed Amber-chrom® (CG 161 cd) (NVM 27%) resin is added to the solution and stirred for 30 minutes adjusting the pH to 4.0-4.2. The resin is filtered off and the spent aqueous solution is assayed for product and stored at 4-8° C. The resin is slurried in 2.0 liters of 20% methanol in water (vol./vol.) The suspension is stirred for 15 minutes adjusting the pH to 4.0-4.2. The resin is again filtered off and the filtrate is assayed for product. The extraction of the resin is repeated 2 more times with 2.0 liters of 20% methanol in water. All the resin extracts and the spent aqueous solution from above were pooled and the pH adjusted to 7-7.2 with 30% ammonium hydroxide. The aqueous solution is extracted with 6×3.0 liters of methylene chloride adjusting the pH to 7.0-7.2 between extractions. The pooled methylene chloride extract is filtered through 250 grams of anhydrous sodium sulfate, concentrated to 500 mL and cooled to 0-3° C. The product crystallized out. The slurry is stirred for 1 hour at 0-3° C. and the solids were filtered and washed with 2×50 mL of cold methylene chloride and dried at 40° C. in vacuum (29 inches of Hg). The weight of solid obtained is 110 grams. The solid obtained can be identified by X-ray powder diffraction as Form I tigecycline. (HPLC area % 97.9, 0.3% epimer).

EXAMPLE 1A

Preparation of Resin from Example 1

The resin of Example 1 is washed prior to use by taking 1 kg of Amberchrom® (CG 161CD from Toso Haas) and slurrying it in 6-7 liters of 12% 2-propanol in water (vol./vol.) and stirring for 12-16 hours. It is filtered and stirred in 6-7 liters of 50% acetonitrile-water (vol./vol.) for 30 minutes. The slurry is filtered and then reslurried in 7 liters of acetonitrile, stirred for 30 minutes, and filtered. The acetonitrile slurry is repeated twice and filtered. The resin is then slurried in 6 liters of methanol, stirred for 1 hour, and filtered. The resin is then slurried in 7 liters of deionized water, stirred for 16 hours, and filtered. The resin is then slurried again in 7 liters of water, stirred for 1 hour, and filtered. The water slurry is repeated 3 more times. The resin is filtered and as much water as possible is removed on the filter funnel for 10-12 hours. It is bottled and stored cold (5-8° C.).

EXAMPLE 2

Preparation of Form 1

10.00 grams of 9-aminominocycline is added portionwise to 60 ml of water at 0-5° C. 10.98 g of t-butylglycine acid chloride hydrochloride is added portionwise keeping the temperature at 0-5° C. After stirring for 40-60 minutes, 30% ammonium hydroxide is added dropwise to the reaction mixture keeping temperature at 0-5° C. to adjust the pH to 7.2. To the solution is added 83 ml of methanol followed by 60 ml of methylene chloride. After stirring for 15 minutes, the phases were separated. The aqueous phase is extracted with 4×40 ml of methylene chloride adjusting the pH to 7.2 before each extraction. To the combined organics is added 10 ml of methanol and the solution is dried over sodium sulfate and then filtered. The solution is concentrated. The resulting suspension is stirred at 5-10° C. for 1 hour and then filtered. The solid is washed with 2×10 mL of cold methylene chloride and then dried to give 8.80 g of product. (Yield 76.8%); Purity by HPLC area % 98.4 and C-4 epimer 0.1%; MS(FAB): m/z 586 (M+H); 585 (M+).

EXAMPLE 3

Preparation of Form II 0.5 g of Form I is slurried in 8 mL of methanol at 22° C. The slurry is warmed to about 35° C. to obtain a clear solution which is cooled to 22° C. and held for 30 minutes to yield a thick red slurry. The slurry is filtered and dried under vacuum at 25° C. overnight. The resulting solid is analyzed by thermal gravimetric analysis ("TGA") and powder X-ray diffraction. The TGA plot (FIG. 8) shows a weight loss of 5.3% at 87° C. and a standard ramp rate of 10° C. per minute is used in the experiment.

Figure 9:
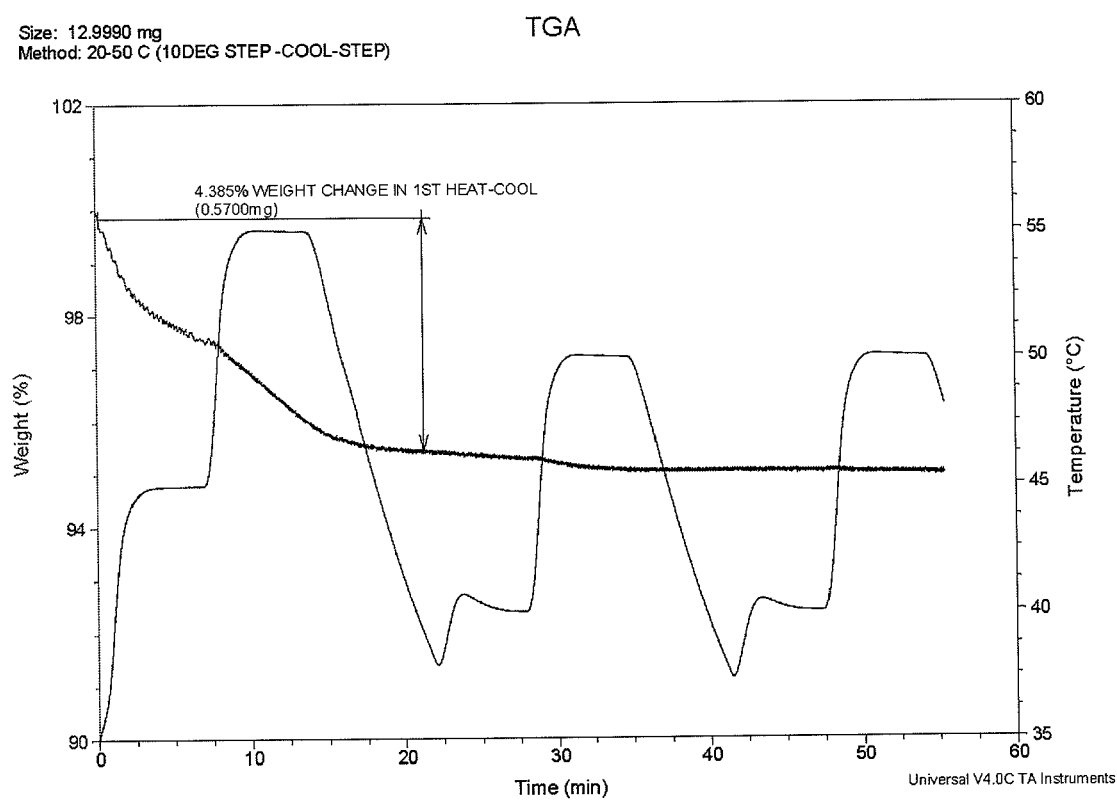
FIG. 9 is a TGA heat-cool cycle of Form II tigecycline.

A heat-cool cycle is run on a fresh sample in a nitrogen atmosphere inside the TGA furnace (FIG. 9). In the first heat-cycle, a 4.4% weight loss is observed which is not observed in the second and third cycles indicating the weight loss is likely water. After the third cycle, the resulting powder is red in appearance.

EXAMPLE 4

Preparation of Form II 30 mg of crude tigecycline is dissolved in 500 μL of deionized water at 40° C. and the solution is stirred at 23° C. To this solution, 500 μL of methanol is added in 100 μL increments over 15 min. After complete addition, a hazy solution is stirred for about 10 min. and then a red crystalline precipitate is obtained. The material is isolated by filtration in air and then dried under vacuum at 40° C. for 8 hours to yield 21.4 mg of Form II as determined by X-ray powder diffraction.

EXAMPLE 5

Preparation of Form II 30 mg of crude tigecycline is dissolved in 500 μL of deionized water at 40° C. and the solution stirred at 23° C. This solution is added to 800 μL methanol and stirred at 10° C. over about 15 minutes. A crystalline precipitate is obtained during addition. The material is isolated by filtration in air and then dried under vacuum at 40° C. for 8 hours to yield 20.2 mg of form II as determined by X-ray powder diffraction.

EXAMPLE 6

Preparation of Form III 0.25 g of Form I is slurried in 2 mL of dichloromethane at 22° C. to form a suspension. 0.01 g of Form V is added as a seed. The suspension is stirred for 96 hours at 22° C. The slurry is subsequently filtered and dried under vacuum at 22° C. The resulting solid Form III is analyzed by hot stage microscopy, X-ray powder diffraction, HPLC (99.98% pure), and optical microscopy.

EXAMPLE 7

Preparation of Form IV 0.15 g of Form I is added to 2 mL of acetonitrile at 22° C. A clear solution is obtained which is stirred for 30 minutes to obtain a suspension. The slurry is filtered and dried under vacuum at 22° C. The resulting off-white solid Form IV is analyzed by hot stage microscopy, X-ray powder diffraction, HPLC (93.39% pure), and optical microscopy.

EXAMPLE 8

Preparation of Form IV 0.167 g of Form I is slurried in acetonitrile at 22° C. The slurry is warmed to 30° C. to obtain a clear solution. 2 mL of n-heptane is added to the solution over the course of 5 minutes. A suspension is formed which is cooled to 22° C. and held at that temperature for 30 minutes. The slurry is filtered and the resulting solid is washed with 5 mL of n-heptane and dried under vacuum at 22° C. The resulting solid Form IV is analyzed by X-ray powder diffraction, HPLC (96.39% pure), and optical microscopy.

EXAMPLE 9

Preparation of Form V 0.22 g of Form I is added to 2 mL of tetrahydrofuran at 22° C. and stirred for 5 minutes. A clear solution is obtained to which 2 mL n-heptane is added. The resulting slurry is stirred at 22° C. for 30 minutes. The slurry is filtered and dried under vacuum at 22° C. The resulting solid Form V is analyzed by hot stage microscopy, X-ray powder diffraction, HPLC (93.57% pure), and optical microscopy.

We claim:

1. A Form I tigecycline having X-ray powder diffraction peaks at about 5.2° 2θ, about 8.3° 2θ, about 11.1° 2θ, and about 24.8° 2θ and having a hot stage melting point onset temperature of about 170° C. to about 172° C.

2. A composition consisting essentially of Form I tigecycline having X-ray powder diffraction peaks at about 5.2° 2θ, about 8.3° 2θ, about 11.1° 2θ, and about 24.8° 2θ and having a hot stage melting point onset temperature of about 170° C. to about 172° C.

3. A process for preparing Form I tigecycline comprising crystallizing tigecycline out of a solution to form a slurry, and filtering the slurry to isolate Form I tigecycline having X-ray powder diffraction peaks at about 5.2° 2θ, about 8.3° 2θ, about 11.1° 2θ, and about 24.8° 2θ and having a hot stage melting point onset temperature of about 170° C. to about 172° C.

4. The process of claim 3 wherein the solution contains methylene chloride.

5. The process of claim 3 further comprising drying the solution prior to the crystallizing step.

6. The process of claim 3 further comprising stirring the slurry prior to the filtering step.

7. The process of claim 3 further comprising combining said Form I tigecycline with at least one pharmaceutically suitable carrier to form a pharmaceutical composition.

8. A pharmaceutical composition made by the process of claim 7.

9. The process of claim 7 further comprising lyophilizing said pharmaceutical composition.

10. A pharmaceutical composition made by the process of claim 9.

* * * * *